(12) United States Patent
Caldwell et al.

(10) Patent No.: US 8,556,839 B2
(45) Date of Patent: Oct. 15, 2013

(54) WALKING DEVICE FOR REMEDYING DROP FOOT

(75) Inventors: Steven Caldwell, Medina, NY (US); Michael J. Caldwell, Medina, NY (US)

(73) Assignee: Caldwell Products, LLC, Medina, NY (US)

( * ) Notice: Subject to any disclaimer, the term of this patent is extended or adjusted under 35 U.S.C. 154(b) by 384 days.

(21) Appl. No.: 12/846,349

(22) Filed: Jul. 29, 2010

(65) Prior Publication Data
US 2012/0029401 A1 Feb. 2, 2012

(51) Int. Cl.
*A61F 5/00* (2006.01)
(52) U.S. Cl.
USPC ............................................ 602/16
(58) Field of Classification Search
USPC .......... 602/28, 29, 23, 5, 1; 36/140, 145, 148, 36/151
See application file for complete search history.

(56) References Cited

U.S. PATENT DOCUMENTS

| | | | |
|---|---|---|---|
| 2,584,010 A | 1/1948 | Goffredo | |
| 2,536,454 A * | 1/1951 | McIntyre | 602/28 |
| 3,527,209 A | 9/1970 | Baker | |
| 3,986,501 A | 10/1976 | Schad | |
| 4,329,982 A | 5/1982 | Heaney | |
| 4,566,447 A | 1/1986 | Deis | |
| 4,817,589 A | 4/1989 | Wertz | |
| 5,277,699 A | 1/1994 | Williamson | |
| 5,382,224 A * | 1/1995 | Spangler | 602/23 |
| 5,860,423 A | 1/1999 | Thompson | |
| 6,102,881 A * | 8/2000 | Quackenbush et al. | 602/28 |
| 6,926,687 B2 | 8/2005 | Shields | |
| 7,458,950 B1 | 12/2008 | Ivany | |
| 7,611,477 B2 | 11/2009 | Dayhoff et al. | |
| 7,674,212 B2 | 3/2010 | Kruijsen et al. | |
| 2003/0073938 A1 | 4/2003 | Crawford et al. | |
| 2005/0043150 A1* | 2/2005 | Nitta et al. | 482/79 |
| 2006/0079822 A1 | 4/2006 | Hjorth | |
| 2010/0042032 A1 | 2/2010 | Tomczak | |
| 2010/0076361 A1 | 3/2010 | Kruijsen et al. | |

FOREIGN PATENT DOCUMENTS

WO 03092560 A1 11/2003

* cited by examiner

*Primary Examiner* — Patricia Bianco
*Assistant Examiner* — Tarla Patel
(74) *Attorney, Agent, or Firm* — Simpson & Simpson, PLLC

(57) ABSTRACT

A walking device for remedying or alleviating symptoms of drop foot, the device wearable with an article of footwear, the device including a backing plate, wherein the backing plate includes an upper portion hingedly secured to a lower portion, a strap secured to the upper portion of the backing plate and extending outwardly therefrom for operatively securing to itself about a leg of a person, a spring including a first end secured to the strap, and a clip secured to a second end of the spring, wherein the clip is operatively arranged to engage with a pair of eyelets for laces of the footwear.

18 Claims, 8 Drawing Sheets

WALKING DEVICE FOR REMEDYING DROP FOOT

FIELD OF THE INVENTION

The invention broadly relates to a walking device, and more specifically, to a device to alleviate drop foot.

BACKGROUND OF THE INVENTION

Drop foot is a neuromuscular disorder characterized by the inability or difficulty of a person to move the ankle and/or lift the toes upward. This particular type of movement is referred to as dorsiflexion. Because of the lack of dorsiflexion, the person with drop foot often drags his foot and toes while walking. Drop foot is also commonly referred to as foot drop.

Some walking aids or devices to alleviate drop foot are known in the art, which provide the person with the ability to control the person's foot to prevent it from dragging across the ground. A problem with many prior walking devices is that they are generally large and bulky, making them difficult to conceal under clothing. Furthermore, many are uncomfortable because they pull on the laces of shoes, or require the user to stand on a plate or other surface, which is inserted into and extends along an insole of a shoe.

Another problem with prior walking devices is that even though prior braces may prevent the person's foot from dragging across the ground, they also limit the mobility of the person's foot and ankle. That is, many such devices lock the user's ankle such that the foot is at a 90 degree angle with respect to the leg, which prevents the toe from dropping, but does not enable the user to walk naturally.

Yet another problem with prior walking devices is that many require extensive modifications to a person's shoe to secure the brace or require the use of a special shoe made specifically for the walking device. This drastically limits the selection of shoe styles available to a person with drop foot. It also prevents a user from being able to put on or take off a walking device at any time desired by the user.

As can be derived from the variety of devices and methods directed at walking devices, many means have been contemplated to accomplish the desired end. Heretofore, tradeoffs were required between preventing the person's toes from dragging due to drop foot, and comfort and mobility (e.g., requiring the user to stand on a plate or platform, by locking the ankle at a specific angle, pulling on shoelaces, etc.). There is also a long-felt need for a walking device which does not require drastic modifications to a person's shoe or the use of a special shoe specifically compatible with the walking device.

BRIEF SUMMARY OF THE INVENTION

The present invention broadly comprises a walking device for remedying or alleviating symptoms of drop foot, the device wearable with an article of footwear, the device including a backing plate, wherein the backing plate includes an upper portion hingedly secured to a lower portion, a strap secured to the upper portion of the backing plate and extending outwardly therefrom for operatively securing to itself about a leg of a person, a spring including a first end secured to the strap, and a clip secured to a second end of the spring, wherein the clip is operatively arranged to engage with a pair of eyelets for laces of the footwear. In one embodiment, the clip is substantially w-shaped. In one embodiment, the device further includes a chain secured between the first end of the spring and the strap, the chain operatively arranged to enable the person to adjust a force exerted by the spring by selectively securing the spring onto any desired link of the chain.

In one embodiment, the clip is operatively arranged to engage in aperture style eyelets. In another embodiment, the clip is operatively arranged to engage in loop-style eyelets. In one embodiment, the device further includes a carabiner clasp for securing the spring to the strap, the spring to the clip, or combinations thereof. In one embodiment, the upper portion and the lower portion are hingedly connected together by a strap hinge. In another embodiment, the upper portion and the lower portion are hingedly connected together by a piece of leather. In another embodiment, the lower portion terminates in a free end which is operatively arranged to be insertable into the footwear behind the leg of the person for enabling the backing plate to extend up from the footwear behind the leg of the person.

The current invention also broadly comprises a walking device for remedying or alleviating symptoms of drop foot, the device wearable with an article of footwear, the device including a backing plate, wherein the backing plate includes an upper portion and a lower portion, the upper portion hingedly secured to the lower portion, wherein the lower portion terminates in a free end which is operatively arranged to be insertable into a footwear for enabling the backing plate to extend up from the footwear behind a leg of a person, a strap secured to the upper portion of the backing plate and extending outwardly therefrom for operatively securing to itself about a leg of a person, a spring including a first end operatively connected to the strap and a second end operatively connected to a portion of the footwear located in front of the leg of the person.

In one embodiment, the device further comprises a clip which is operatively arranged to engage in a pair of eyelet holes for laces of the footwear. In one embodiment, the device further comprises a clip which is operatively arranged to engage in a pair loops for laces of the footwear. In another embodiment, the device further comprises a clip which is operatively arranged to engage below flaps formed in the footwear proximate to hook-and-loop style straps for tightening the footwear. In another embodiment, the device further comprises a harness secured about the footwear, the harness operatively arranged for engaging with the second end of the spring.

The current invention also broadly comprises a walking device including a backing plate, wherein the backing plate includes an upper portion and a lower portion, the upper portion hingedly secured to the lower portion, a strap secured to the upper portion of the backing plate and extending outwardly therefrom and securable about a leg of a person, a spring, wherein the spring includes a first end secured to the strap, and a harness secured to a second end of the spring, wherein the harness is operatively arranged to enclose the footwear. In one embodiment, the harness comprises a toe strap wrapped around a width of the footwear, a lateral strap affixed at both ends to the toe strap, the lateral strap wrapping around a back of the footwear, and at least one front strap extending in front of the footwear and connected at both ends to the toe strap. In another embodiment, the toe strap includes an anchor ring for engaging with the second end of the spring.

It is a general object of the present invention to provide a walking device in a compact form so that the walking device may be more easily concealed.

It is another general object of the present invention to provide a walking device which does not limit the mobility or rotation of a user's ankle.

It is yet another object of the present invention to provide a walking device can easily be secured and removed from a person's everyday shoe without requiring drastic modifications to the shoe or a special shoe that is made to be compatible with the walking device.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "substantially" is synonymous with terms such as "nearly", "very nearly about", "approximately", "around", "bordering on", "close to", "essentially", "in the neighborhood of", "in the vicinity of", etc., and such terms may be used interchangeably as appearing in the specification and claims. As used herein, the term "shoe" means any type of shoe, boot, or other footwear, including, but not limited to running shoes, walking shoes, tennis shoes, sandals, dress shoes, loafers, sneakers, basketball shoes, slippers, hiking boots, work boots, galoshes, etc. Furthermore, as used herein, "person" may be used interchangeably with "user", especially to signify a person wearing an apparatus according to the current invention. Although any methods, devices or materials similar or equivalent to those described herein can be used in the practice or testing of the invention, the preferred methods, devices, and materials are now described.

Figure 1:
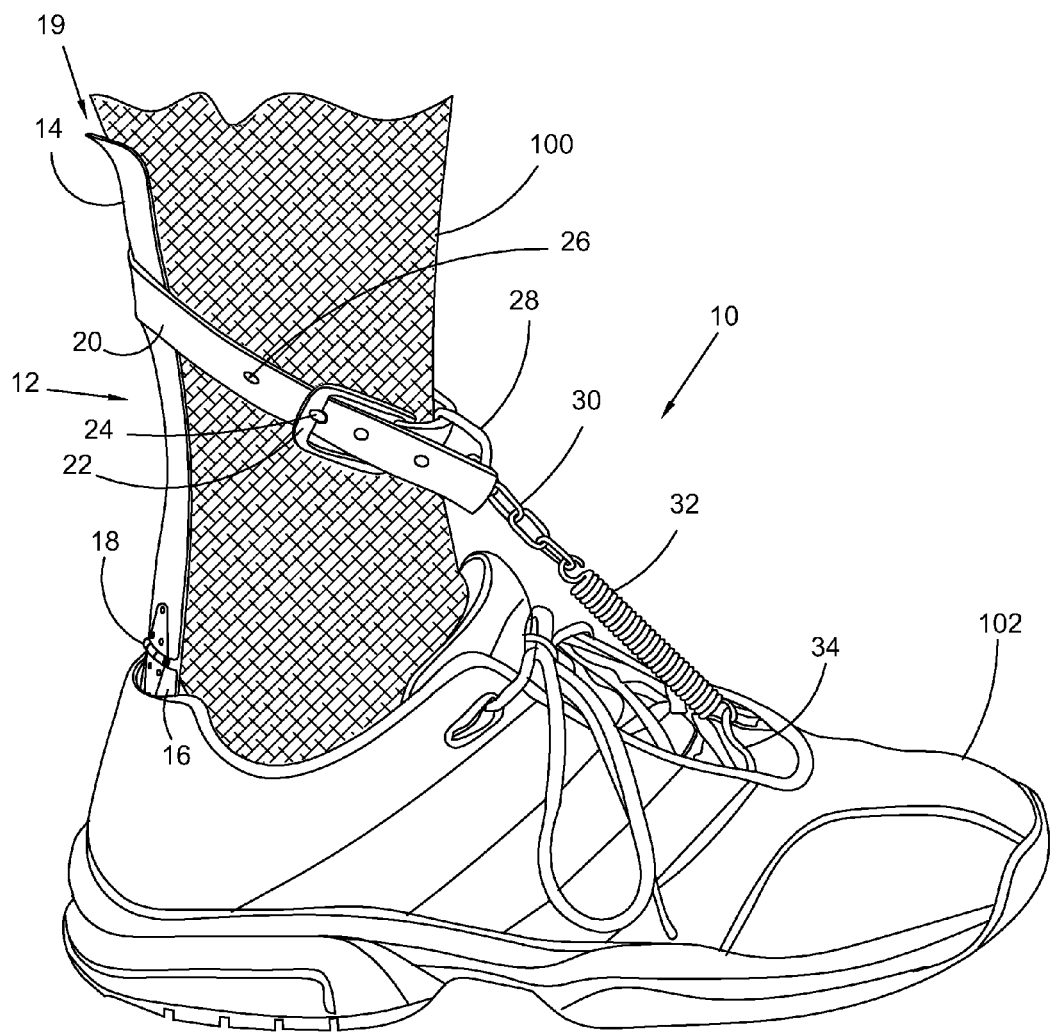
FIG. 1 is a side perspective view of a first embodiment of the present invention.
Figure 2:
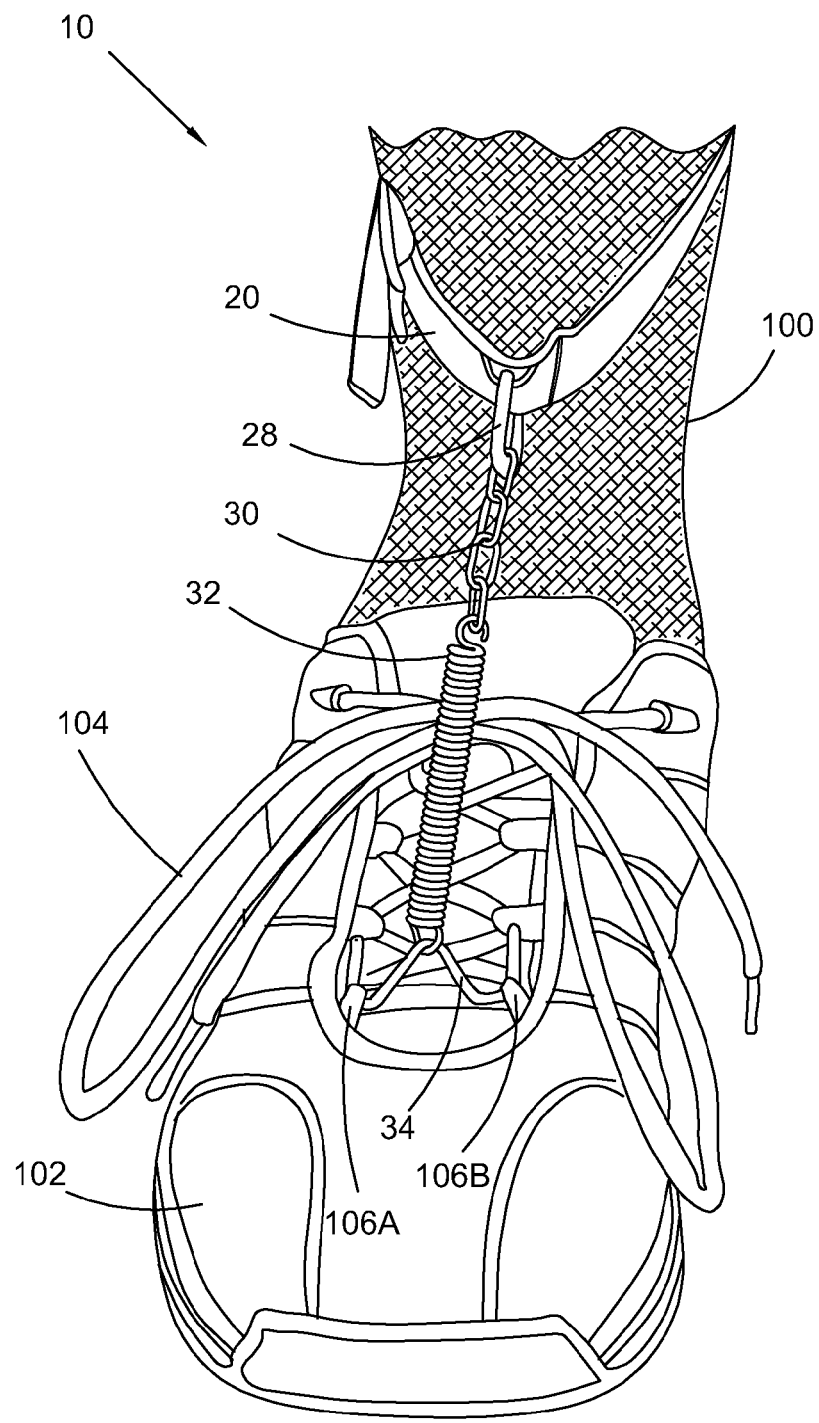
FIG. 2 is a front perspective view of the walking device shown in FIG. 1.

Referring now to the figures, FIGS. 1 and 2 show perspective views of one embodiment of walking device 10. Backing plate 12 includes upper portion 14 and lower portion 16. Upper portion 14 is secured to lower portion 16 via hinge 18. The upper portion extends up along the length of leg 100 of a user. In the shown embodiment, the upper most edge 19 of portion 14 is flared out and back away from user's leg 100. The flared end is included such that the calf muscle of the user can comfortably flex and move with respect to the backing plate while the user is walking, without the backing plate protruding into the calf of the user. In addition to the flaring back away from the user's leg, the backing plate is also gently rounded so that it wraps slightly around the sides of user's leg. The amount of roundedness of the backing plate could vary, but should generally match the contours of an average human leg or the roundedness of the back of a shoe.

Lower portion 16 is arranged to be inserted into shoe 102 between the heel of the user and the back of shoe 102, and the roundedness enables the lower portion to fit snugly and comfortably between a user's heel and the shoe. The lower portion is preferably inserted into the shoe until it contacts the insole of the shoe. When contacting the insole of the shoe, lower portion 16 should be configured to have a height corresponding to a depth of the shoe, in order to extend to a point at or above the top edge of the shoe. By the depth of the shoe, it is meant the distance between the insole of the shoe and the top edge of the shoe. For example, as shown, the lower portion of the backing plate extends just above the back of the shoe so that the hinge is located just above the back of shoe 102, such that the shoe does not interfere with the rotation of hinge 18. Advantageously, hinge 18 enables the user's foot, leg, and ankle to move through a full range of motion and does not lock the ankle into place. Also, as shown in more detail below, lower portion 16 terminates in a free end which is simply inserted into shoe 102 and does not need to be held down by the user standing on the plate or another component connected to the backing plate.

As one specific example, it has been found that for a typical male user, the lower portion is approximately a two inch by three inch plate, and the upper portion is approximately a seven inch long plate that widens from two includes wide at the bottom (where the hinge is affixed) to three and one quarter inches at the top, where flared edge 19 is located. The backing plate is preferably made from metal, but it should be recognized that hard plastics or other rigid materials could work sufficiently well, as desired. It should be appreciated that different sizes and materials are within the scope and spirit of the current invention.

Strap 20 is secured to upper portion 14 of backing plate 12 and extends outwardly therefrom to secure about leg 100 of the user. Strap 20 is releasably and adjustably securable about the leg of the user via buckle 22, which includes prong 24 that is selectably insertable into apertures 26. It should be appreciated that any other means known in the art could be used to secure the strap about the leg of a user, such by use of hook and loop type material, a double D-ring configuration, or any other style of snaps, buckles, or the like. Furthermore, strap 20 could be manufactured from any suitable material, such as nylon, leather, fabric, etc. It has been found that device 10 is most comfortably worn when strap 20 is not tightly secured about the leg of the user. For example, as shown, there is a slight gap between the strap and the user's leg and the strap sags slightly downward. Thus, it is suggested to include a space, such as the width of two fingers, between the user's leg and the strap when securing the strap in place (e.g., a user could insert two fingers between the strap and the user's leg while fastening the ends of the strap together). If the strap is too tight, it will tend to pinch or cut into the user, especially when the calf muscle flexes when walking.

In the shown embodiment, anchor ring 28 is secured to the front of the strap and also to chain 30. In some embodiments, spring 32 may be connected directly to ring 28 or to strap 20. Spring 32 is shown as a coil spring, but it should be appreciated that bungees or other elastic cords could replace the spring, and that any such alternative is considered a spring for the purposes of this disclosure. In the shown embodiment, chain 30 is included to provide adjustability to the tightness of spring 32. As is known by Hooke's law, the force exerted by a spring is directly proportional to the displacement of the spring from its resting position. Therefore, chain 30 enables one end of spring 32 to be selectively secured at different displacements of the spring so that the user can change the force of the spring on-the-fly as desired. Furthermore, it should be appreciated that chain 30 provides additional adjustability to enable the same device 10 to be used on a variety of different shoes of different lengths or having eyelets in different positions. The opposite end of spring 32 is secured to clip 34. Clip 34 is includes a v-shaped bend for engaging with the spring, and is operatively arranged to insert into a pair of eyelets of the shoe. In the shown embodiment, the eyelets comprise loops through which laces 104 of the shoe are threaded. It should also be appreciated that chain 30 and spring 32 could be swapped in their arrangement so that the chain is instead connected to clip 34, or so that there is a chain on both sides of the spring for even greater adjustability.

It has been found that it is easiest to affix the spring between the strap and the clip by bending down and rotating the user's leg forward toward the user's foot such that the spring compresses to its rest position, making it easier to extend the spring in order to engage both ends of the spring. As the user stands, the user's leg will rotate away from the user's foot, and the spring will pull the user's foot up towards the user's leg. Thus, when the user lifts his foot off the ground while walking, the toes of the user's foot will automatically be lifted and rotated upwards. In this way, the user can utilize the spring to perform the lifting/rotating motion that is otherwise not possible with drop foot symptoms, and therefore walk with a natural gait while avoiding dragging the user's toes. This also enables the user to perform other tasks which would otherwise have been difficult or impossible, such as operating the pedals of an automobile, sewing machine, piano, etc. It should also be appreciated that since pants are commonly worn such that they have legs that extend down over the laces of shoes or other footwear, the device can almost entirely be concealed under an ordinary pair of pants, if desired.

Figure 3:
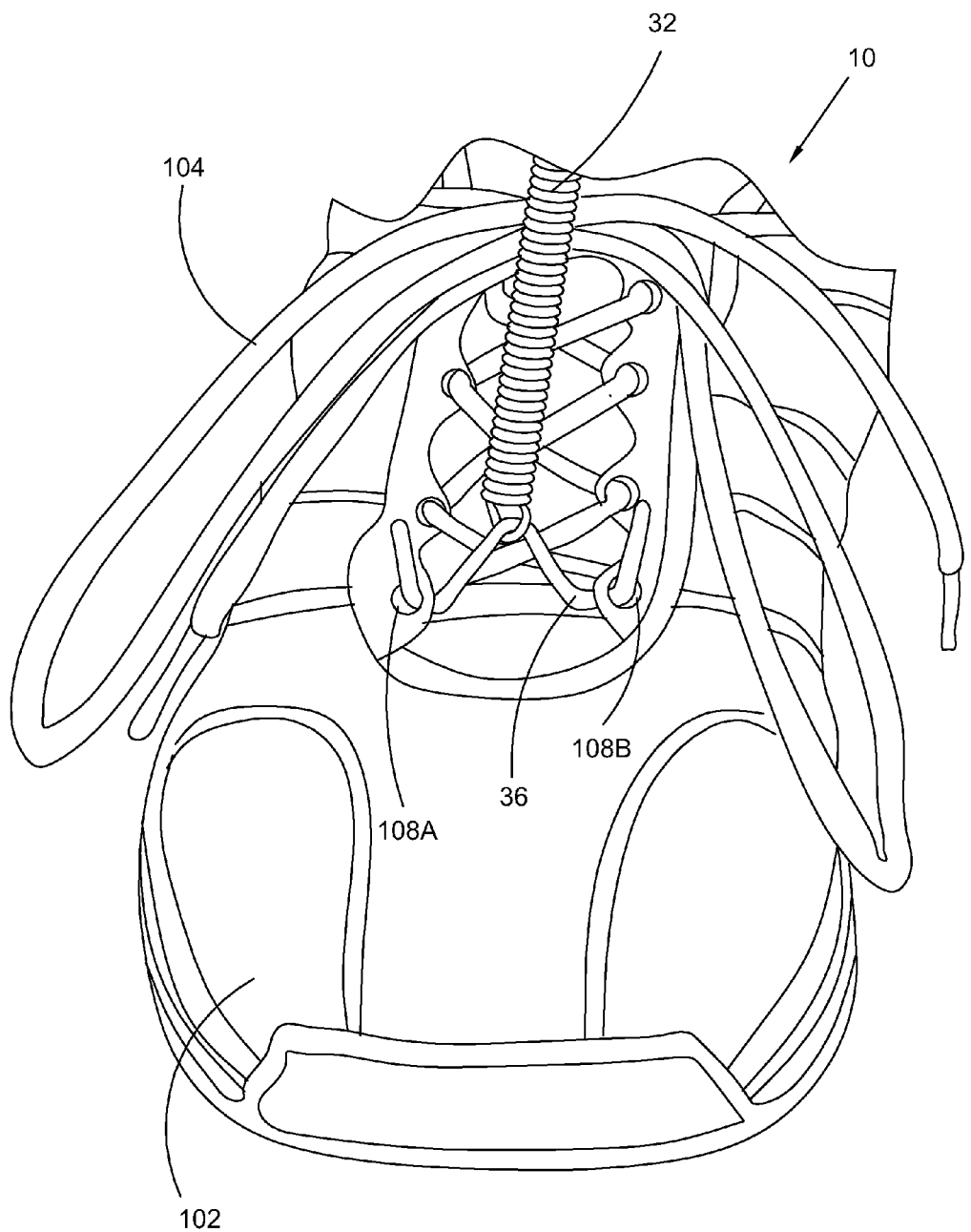
FIG. 3 is a front perspective view of a second embodiment of the walking device, depicting a spring secured to a clip that is inserted into the eyelets of the shoe.

In FIG. 2, the eyelets of the shoe comprise loops 106A and 106B through which the laces 104 are threaded. In FIG. 3, the laces and clip 36 are instead threaded through eyelet holes 108A and 108B. Clip 34 and clip 36 may be substantially identical in some embodiments.

Figure 4:
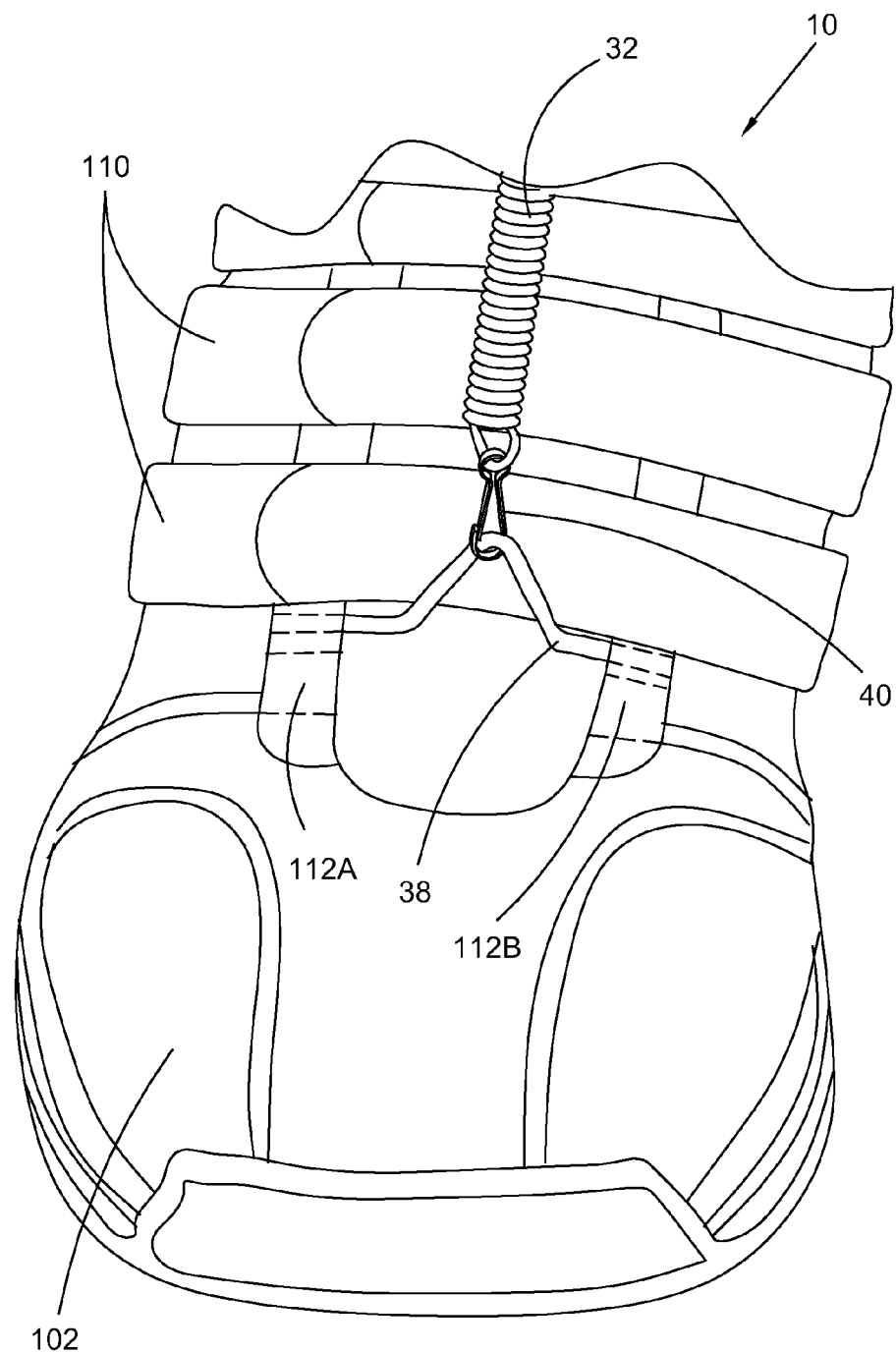
FIG. 4 is a front perspective view of a third embodiment of the present invention.

In other embodiments, clip 36 may be substantially flat, aligned in only a single plane, while clip 34 may include bends in additional planes in order to more to more securely grip through loops 106A and 106B. For example, the v-shaped portion of clip 34 which engages with the spring may be in a first plane, while the legs which extend from the v-shaped portion are first bent in towards the shoe for passage through loops 106A and 106B, and next bent to point in a generally upwards direction for preventing the clip from becoming disengaged from the spring. Despite any differences, it can be seen that both clips 34 and 36 include a v-shaped bend for engaging with spring 32. A third embodiment is shown in FIG. 4, which also shares the v-shaped bend for engaging with the spring. In this embodiment, the shoe does not have laces, but instead includes straps 110 that are securable together by hook-and-loop type material. Clip 38 includes a v-shaped bend, like clips 34 and 36, for engaging with spring 32. The ends or legs of clip 38 extend straight out from the v-shaped bend and are held down between the tongue of the shoe and flaps 112A and 112B, by straps 110. That is, the pressure caused tightening straps 110 securely holds the clip in place under side flaps 112A and 112B against the user's foot and/or the tongue of the shoe. In this embodiment, spring 32 is shown connectable to the clip not directly, but instead by clasp 40. In the shown embodiment, clasp 40 takes the form of a non-locking carabiner. It should be appreciated that clasp 40 could be used in any of the embodiments discussed herein to secure clips 34, 36, or 38 to the spring, the spring to chain 30, chain 30 to anchor ring 28, etc. Thus, the carabiner or clasp may be utilized by users who have difficulty engaging and disengaging the elements of the current invention. It should be further appreciated that in the embodiments shown in FIGS. 2, 3, and 4, device 10 includes backing plate 12, strap 20, and the other elements connected to spring 32 and installed into shoe 102, as described generally herein.

Thus, it should be appreciated that clips 34, 36, and 38 each include a v-shaped portion which extends upwards for engagement with spring 32. Furthermore, the clips 34, 36, and 38 are operatively arranged having legs which are bent or shaped to engage with the tightening means of the shoe. By tightening means, it is meant the structure or portion of the structure of a shoe or piece of footwear which enables the user to tighten the shoe (e.g., hook-and-loop straps for holding down flaps, eyelet holes through which laces are threaded, loops through which laces are threaded, etc.).

Figure 5:
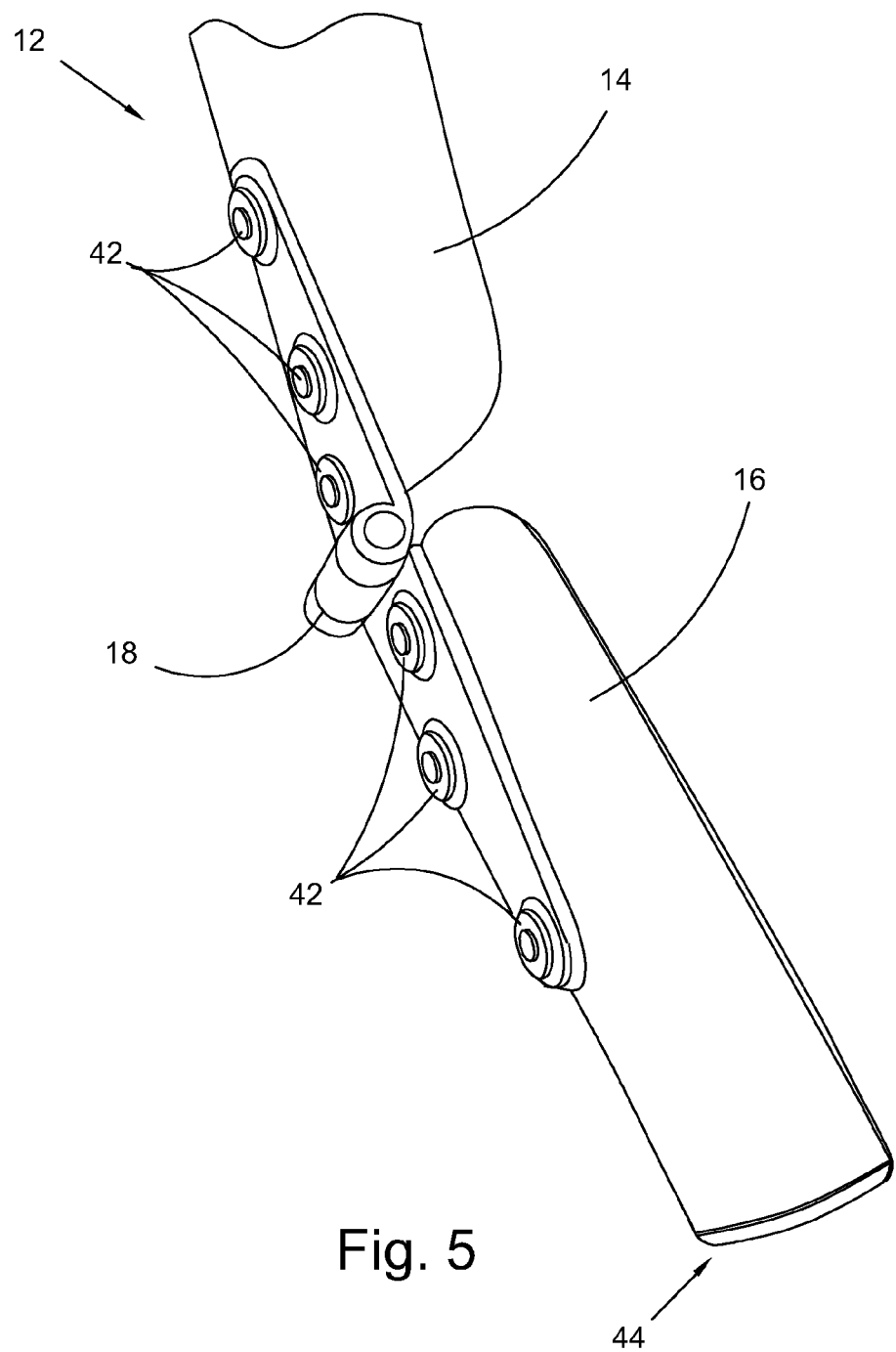
FIG. 5 is a perspective view of the backing plate having a strap hinge.

One style of hinge for backing plate 12 is shown in FIG. 5. This style of hinge is generally referred to as a strap hinge, and is also shown in FIG. 1. In this embodiment, upper portion 14 is secured to lower portion 16 via hinge 18. The hinge is secured to the upper and lower portions, for example, by rivets 42. As also shown in this Figure, lower portion 16 terminates in free end 44. It has been found that rolling or bending the free end back on itself, as shown, results in a thicker rounded edge which does not tear, cut, or ruin the insole of a user's shoe. Furthermore, as discussed above, the free end enables a user to selectively install and uninstall device 10 without requiring the user to take off his shoe, since the backing plate is not affixed to the shoe, and since the user is not required to stand on a portion of the backing plate or a component connected to the backing plate. As discussed above, the lower portion should be rounded to wrap slightly around the sides of the user's foot so that the lower portion fits snugly between the user's heel and/or leg and the user's shoe. Advantageously, in addition to gravity, the force exerted by the spring on the strap, and therefore on backing plate, in a generally downward direction also helps to prevent the free end of the lower portion of the backing plate from inadvertently popping out of the shoe. Also, the corners at edge 44 should also be rounded so that they do not catch on the insole of the shoe or socks of the user. Further, by rounding the corners and edge 44 itself, the backing plate can float slightly up and down and swivel slightly side to side about the heel of the user, which accommodates a fuller range of motion of the user, unlike many prior art devices which tend to lock the user's ankle or otherwise limits mobility.

Figure 6:
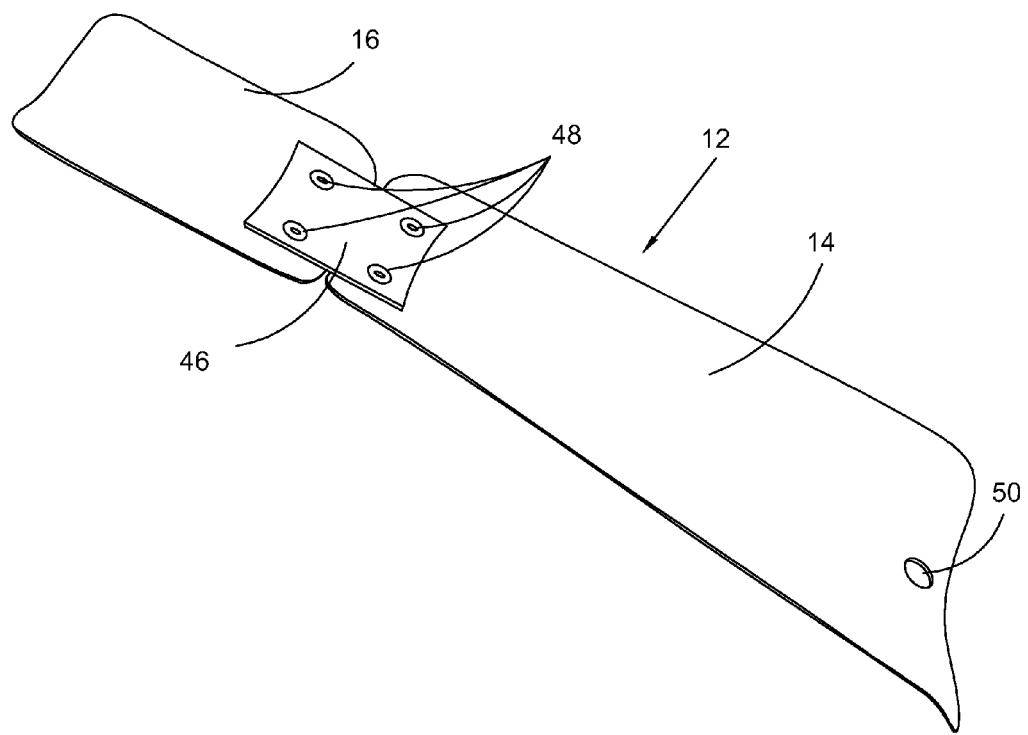
FIG. 6 is a perspective view of the backing plate having a hinge made of a resilient material.

A second style of hinge is shown in FIG. 6. In this embodiment, the hinge comprises hinge member 46, which is a square, patch, or piece of resilient, but semi-rigid material. It has been found that a piece of leather or similar material works suitably for hinge member 46, since it enables the rotation upper and lower portions of the backing plate with respect to each other, while also providing sufficient rigidity so that the upper portion does not collapse down onto the lower portion. Unlike hinge 18, hinge member 46 may be installed on the side of the backing plate which faces the leg and heel of the user, as shown. The hinge member may be included by any means known in the art, such as rivets 48. In this Figure, opening 50 is also shown proximate top edge 19 of upper portion 14 of the backing plate. As described in more detail below, opening 50 is utilized in some embodiments, for example, to secure strap 20 to the backing plate with a rivet or the like.

Figure 7:
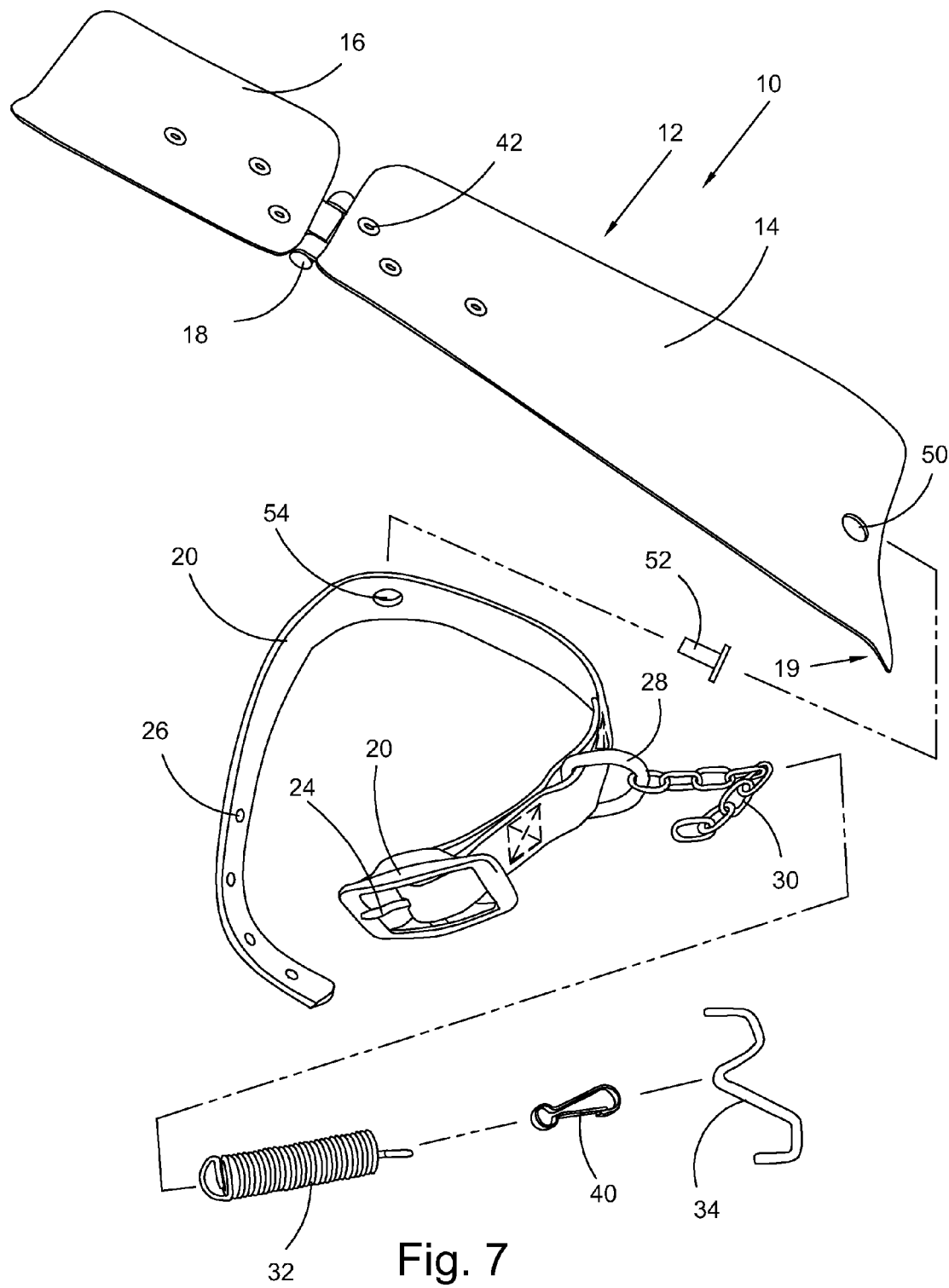
FIG. 7 is an exploded view of one embodiment of the present invention.

FIG. 7 is an exploded view of one embodiment of walking device 10. In the shown embodiment, upper portion 14 is connected to lower portion 16 via hinge 18, such as shown in FIGS. 1 and 5. In this embodiment, it can again be seen that upper edge 19 of the backing plate flares out and back in order to accommodate a user's calf. It can also be seen that the upper and lower portions of the backing plate has a curvature about its longitudinal axis so that it fits snugly about the back of the user's leg and partially wraps around the sides of the user's leg, heel, and/or foot. It can be seen that rivet 52 is used to attach backing plate 12 to strap 20. Openings 50 and 54 may be included in the backing plate and strap, respectively, to facilitate the fastening of the strap to the plate with a rivet. If one such rivet or pin is used, as shown, it should be appreciated that strap 20, before being secured about a user's leg, can be rotated about the single rivet such that buckle 22 is positionable on either side of the backing plate. For example, this would enable a single walking device 10 to be used on either the left or right leg of a user, with the buckles selectively facing out or in, as preferred by the user. As discussed above, chain 30 is affixed to anchor ring 28 of the strap, with the chain enabling a user to selectively determine the tension or force to be exerted by the spring by attaching the spring to any of the links of the chain to set the desired tension of the spring. That is, by selecting links of chain 30 which are closer to or farther away from the opposite anchor point (e.g., clips 34, 36, or 38), the user can set the displacement of the spring, which changes the force exerted by the spring. Any extra links of chain 30 can simply hang loosely. Spring 32 is connected between clip 36 and either chain 30 or ring 28. In the shown embodiment, carabiner 40 is included between clip 36 and spring 32 in order to facilitate the connection of the spring to the clip by reducing the distance the spring would need to be stretched in order to secure the end of the spring to the clip.

Figure 8:
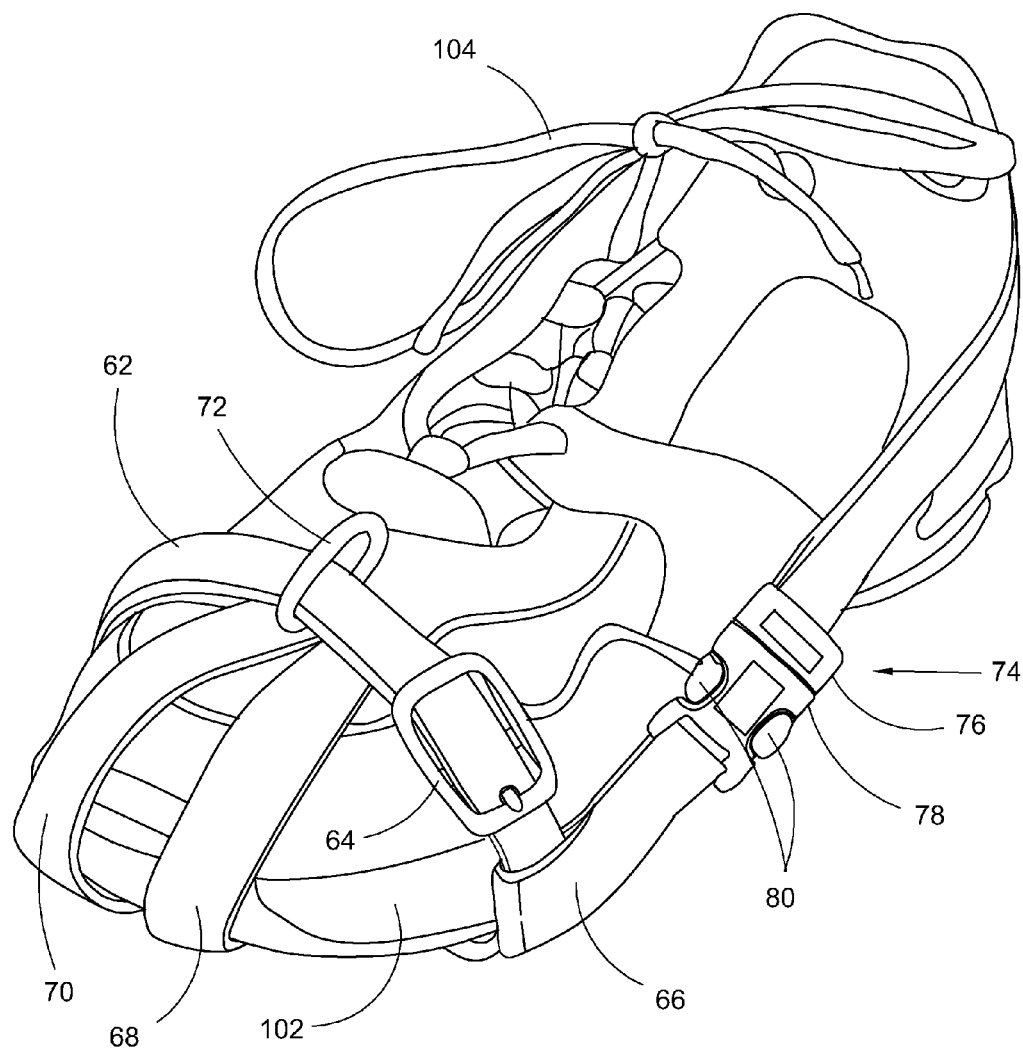
FIG. 8 is a perspective view of a yet another embodiment of the present invention.

FIG. 8 is a perspective view of another embodiment of walking device 10. This embodiment is intended to be used without any of clips 34, 36, or 38. Therefore, it can be used with a shoe having laces 104, or with a laceless shoe. In this embodiment, a harness is formed by toe strap 62 that is wrapped entirely around the width of the front or toe box of shoe 102. In the shown embodiment, the toe strap is adjustable or releasable via buckle 64, which substantially resembles buckle 22, discussed above. In order to prevent the harness from slipping forward off the shoe, front straps 68 and 70 are included, secured at both ends to strap 62 (the bottom connections to toe strap 62 hidden under the shoe). In the shown embodiment, front straps 68 and 70 are included, although it should be appreciated that a single strap or more than two such straps could be used in other embodiments. Lateral strap 66 is secured to toe strap 62, as shown, and looped around the back of the shoe, where the lateral strap connects to the other side of the toe strap (this connection hidden behind the shoe). Ring 72 is included in lieu of clips 34, 36, or 38 to receive spring 32. In order to facilitate the installation of the harness onto a shoe, buckle 74 can be included for splitting strap 66 into two portions. This type of buckle is known, but is described generally below for completeness. Buckle 74 includes male portion 76 which is insertable into female portion 78. Tabs 80 are part of the male portion and are spring-loaded such that they lock with female portion 78 upon insertion of male portion 76.

The male and female portions can be disconnected by squeezing tabs 80 inwards and pulling the male and female portions apart. It should be appreciated that while clips 34, 36, or 38 are not used in this embodiment, the remaining components discussed above, such as backing plate 20, buckle 22, anchor ring 28, chain 30, and spring 32 would all be similarly arranged and utilized in the embodiment of FIG. 8 as these components were discussed with respect to FIGS. 1-7, but with spring 32 engaged with ring 72 instead of clips 34, 36, or 38. Thus, like the embodiments described with respect to FIGS. 1-7, the embodiment illustrated in FIG. 8 can also be quickly and easily put on or taken off without the need for the user to take off shoe 102.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What we claim is:

1. A walking device for remedying or alleviating symptoms of drop foot, said device wearable with an article of footwear, said device comprising:
    a backing plate consisting of: an upper portion hingedly secured to a lower portion;
    a strap secured to said upper portion of said backing plate and extending outwardly therefrom for operatively securing to itself about a leg of a person;
    a spring including a first end secured to said strap; and,
    a clip secured to a second end of said spring, wherein said clip is operatively arranged to engage with a pair of eyelets for laces of said footwear, wherein said clip is substantially w-shaped.

2. The walking device of claim 1, further including a chain secured between said first end of said spring and said strap, said chain operatively arranged to enable said person to adjust a force exerted by said spring by selectively securing said spring onto any desired link of said chain.

3. The walking device of claim 1, wherein said clip is operatively arranged to engage in aperture style eyelets.

4. The walking device of claim 1, wherein said clip is operatively arranged to engage in loop-style eyelets.

5. The walking device of claim 1, further including a carabiner clasp for securing said spring to said strap, said spring to said clip, or combinations thereof.

6. The walking device of claim 1, wherein said upper portion and said lower portion are hingedly connected together by a strap hinge.

7. The walking device of claim 1, wherein said upper portion and said lower portion are hingedly connected together by a piece of leather.

8. The walking device of claim 1, wherein said lower portion terminates in a free end which is operatively arranged to be insertable into said footwear behind said leg of said person for enabling said backing plate to extend up from said footwear behind said leg of said person.

9. The walking device of claim 1, wherein one only single strap is secured to the upper portion.

10. The walking device of claim 1, wherein one only single spring is secured to the strap.

11. A walking device for remedying or alleviating symptoms of drop foot, said device attachable to a leg of a person and wearable with an article of footwear on a foot of the person, said device comprising:
- a backing plate, wherein said backing plate includes an upper portion and a lower portion, said upper portion hingedly secured to said lower portion, wherein said lower portion terminates in a free end which is operatively arranged to be insertable into the article of footwear between the article of footwear and a heel of the foot of the person for enabling said backing plate to extend up from said article of footwear behind the leg of the person;
- a strap secured to said upper portion of said backing plate and extending outwardly therefrom for operatively securing to itself about the leg of the person;
- a spring including a first end operatively connected to said strap and a second end operatively connected to a portion of said footwear located in front of said leg of said person.

12. The walking device of claim 11, wherein said device further comprises a clip which is operatively arranged to engage in a pair of eyelet holes for laces of said footwear.

13. The walking device of claim 11, wherein said device further comprises a clip which is operatively arranged to engage in a pair loops for laces of said footwear.

14. The walking device of claim 11, wherein said device further comprises a clip which is operatively arranged to engage below flaps formed in said footwear proximate to hook-and-loop style straps for tightening said footwear.

15. The walking device of claim 11, further comprising a harness secured about said footwear, said harness operatively arranged for engaging with said second end of said spring.

16. The walking device of claim 11, wherein the backing plate consists of a single upper portion hingedly connected to a single lower portion.

17. The walking device of claim 11, wherein one only single spring is secured to the strap.

18. A walking device attachable to a leg of a person, comprising:
- an article of footwear;
- a hinge;
- a backing plate including:
  - an upper portion fixedly secured to the hinge and arranged to be placed along a back of the leg; and,
  - a lower portion:
    - fixedly secured to the hinge; and,
    - arranged to be inserted in the article of footwear between the article of footwear and a heel of the foot;
- a strap directly connected to the upper portion and arranged to wrap about the leg; and,
- a spring with:
  - a first end connected to a portion of the strap; and,
  - a second end arranged to engage the article of footwear.

* * * * *